(12) United States Patent
Hanaoka et al.

(10) Patent No.: US 8,094,278 B2
(45) Date of Patent: Jan. 10, 2012

(54) LIQUID CRYSTAL DISPLAY DEVICE

(75) Inventors: Kazutaka Hanaoka, Tenri (JP);
Kunihiro Tashiro, Matsusaka (JP);
Takashi Sasabayashi, Kounosu (JP);
Katsufumi Ohmuro, Atsugi (JP)

(73) Assignee: Sharp Kabushiki Kaisha, Osaka (JP)

( * ) Notice: Subject to any disclaimer, the term of this patent is extended or adjusted under 35 U.S.C. 154(b) by 488 days.

(21) Appl. No.: 11/667,014

(22) PCT Filed: Nov. 24, 2005

(86) PCT No.: PCT/JP2005/021574
§ 371 (c)(1),
(2), (4) Date: Sep. 16, 2008

(87) PCT Pub. No.: WO2006/057295
PCT Pub. Date: Jun. 1, 2006

(65) Prior Publication Data
US 2009/0015772 A1    Jan. 15, 2009

(30) Foreign Application Priority Data
Nov. 24, 2004 (JP) .................................. 2004-339566

(51) Int. Cl.
*G02F 1/1337* (2006.01)
(52) U.S. Cl. ........................................ 349/130; 349/123
(58) Field of Classification Search .................. None
See application file for complete search history.

(56) References Cited

U.S. PATENT DOCUMENTS

| | | | |
|---|---|---|---|
| 5,668,651 A | 9/1997 | Yamada et al. | |
| 5,769,393 A * | 6/1998 | Kobayashi et al. | 252/299.01 |
| 6,061,116 A | 5/2000 | Nishida et al. | |
| 6,512,569 B1 | 1/2003 | Acosta et al. | |
| 2001/0030732 A1* | 10/2001 | Tanabe et al. | 349/201 |
| 2002/0167631 A1* | 11/2002 | Ishihara et al. | 349/123 |
| 2003/0048401 A1 | 3/2003 | Hanaoka et al. | |
| 2004/0010699 A1* | 1/2004 | Shao et al. | 713/189 |
| 2005/0200789 A1* | 9/2005 | Nakanishi | 349/139 |

FOREIGN PATENT DOCUMENTS

| | | |
|---|---|---|
| JP | 8-152609 A | 6/1995 |
| JP | 8-152609 A | 6/1996 |
| JP | 2002-357830 A | 12/2002 |
| JP | 2003-43474 A | 2/2003 |
| JP | 2004-219948 A | 8/2004 |
| KR | 2000-0029192 A | 5/2000 |
| WO | 97/12275 A1 | 4/1997 |

OTHER PUBLICATIONS

Korean Office Action mailed Feb. 26, 2008 in corresponding Korean application 9-5-2008-010202672.

* cited by examiner

*Primary Examiner* — Tina Wong
(74) *Attorney, Agent, or Firm* — Nixon & Vanderhye P.C.

(57) ABSTRACT

The present liquid crystal display is obtained by disposing, between two parallel substrates on which a pair of electrodes are formed, two alignment control films, and a liquid crystal composition comprising a liquid crystal and a polymerizable compound that can be polymerized by light, a heat or a combination thereof, and then polymerizing the polymerizable compound. If the liquid crystal to be used is one having a negative dielectric constant anisotropy, the alignment control films are vertical alignment control films having been subjected to rubbing processing so that the rubbing directions are parallel to each other, and when voltage is not applied, only liquid crystal molecules in a specific area in a pixel present the splay alignment. According to the present invention, a liquid crystal display device having a high-speed response can be implemented.

9 Claims, 13 Drawing Sheets

ULTRAVIOLET RAYS

LIQUID CRYSTAL DISPLAY DEVICE

This application is the U.S. national phase of international application PCT/JP2005/021574 filed 24 Nov. 2005 which designated the U.S. and claims benefit of JP 2004-339566, dated 24 Nov. 2004, the entire content of which is hereby incorporated by reference.

BACKGROUND OF THE INVENTION

1. Field of the Invention

The present invention relates to a liquid crystal display device.

2. Description of the Related Art

As the applications of liquid crystal devices to TV increase, the demand for liquid crystal display devices which respond at a high-speed to handle moving pictures is progressively increasing. Some high-speed response liquid crystal display devices use ferroelectric liquid crystals. But there are many problems with ferroelectric liquid crystals, including difficulties in maintaining a stable layer structure.

Modes for implementing a high-speed response using a nematic liquid crystal include an OCB (Optically Compensated Bend) mode and an OCS (Optically Compensated Splay) mode. According to these modes, the rubbing directions of both substrates are the same, and the alignment of liquid crystal molecules is formed such that the splay state becomes a lower energy state in the horizontal alignment and the bend state becomes a lower energy state in the vertical alignment, and these alignment states are each reversed by applying a predetermined voltage $V_{cr}$ or higher. In other words, if liquid crystal molecules are aligned horizontally when voltage is not applied, the bend (OCB) state is implemented by applying voltage, and if liquid crystal molecules are aligned vertically when voltage is not applied, the splay (OCS) state is implemented by applying voltage. In these modes, if the liquid crystal molecules have been maintained to be OCB or OCS, the alignment change speed of the liquid crystal molecules thereafter can be made large, and therefore the response time of the display can be decreased to be extremely short.

In this way, OCB and OCS modes have a feature where the response time is very short in the change of all the grayscales, and exhibit high expectations in applications to TV. However, these alignment states return to their original alignment states where the liquid crystal molecules are stable in energy, if the voltage is lower than $V_{cr}$. From this original alignment, the alignment change speed of the liquid crystal molecules decreases, and the response time for a display cannot be decreased.

Therefore a voltage not less than a predetermined voltage $V_{cr}$ must be applied continuously as long as the liquid crystal display device is in use, so that alignment does not return to the original alignment. Otherwise, alignment must be quickly shifted to the required alignment when the display device is turned ON.

A method to solve this problem is to add a photo-polymerizable monomer to the liquid crystal, and apply a voltage not less than $V_{cr}$ in order to change the alignment state of the liquid crystal molecules (hereafter changing the alignment state may be called "alignment transition"), then fix the alignment state by irradiating ultraviolet rays (e.g. Japanese Patent Application Laid-Open No. 2003-43474 (Claims)).

Figure 1A:
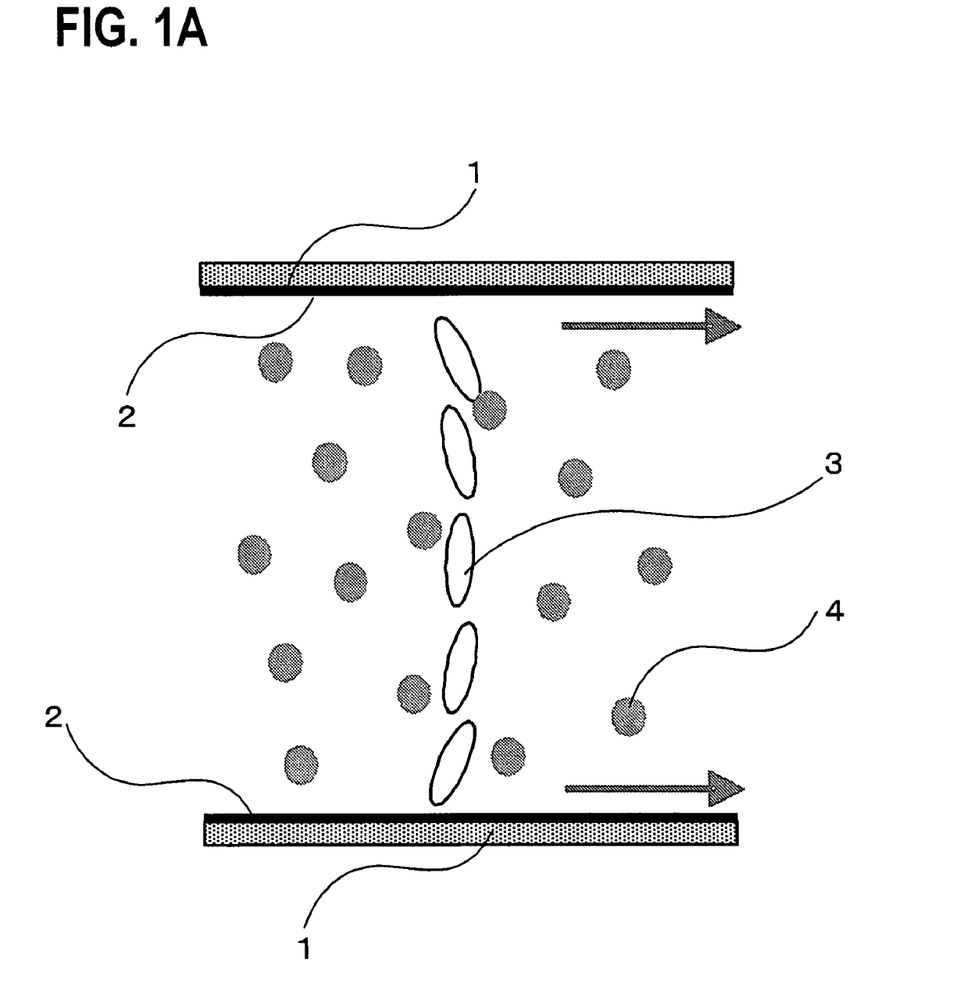
FIG. 1A is a schematic cross-sectional side view depicting liquid crystal molecules in the bend state in a liquid crystal display panel.

This method will be described with reference to FIGS. 1A, 1B and 1C. FIG. 1A is a cross-sectional view of a liquid crystal display panel viewed from the side when a pair of vertical alignment control films 2 are formed on a pair of substrates 1, and have been rubbed so that the rubbing directions are parallel to each other, between which a liquid crystal composition comprising a liquid crystal 3 having a negative dielectric constant anisotropy and a polymerizable compound 4 which can be polymerized by light, heat or a combination thereof is filled. In FIG. 1A, the arrows indicate the rubbing direction. In this case, voltage is not applied between the substrates 1. In this state, the liquid crystal molecules 3 are in the bend state, as shown in FIG. 1A.

Figure 1B:
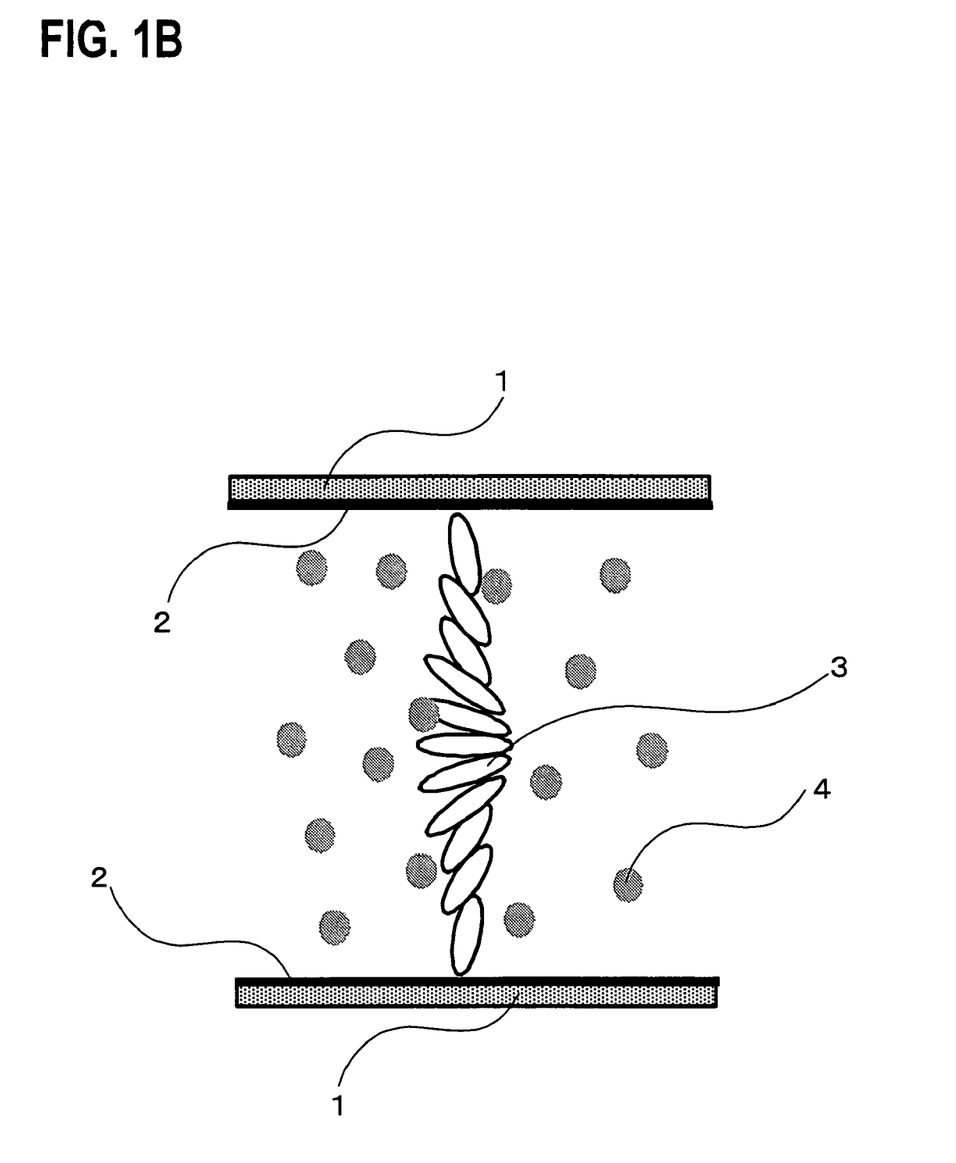
FIG. 1B is a schematic cross-sectional side view depicting liquid crystal molecules in the splay state in a liquid crystal display panel.
Figure 1C:
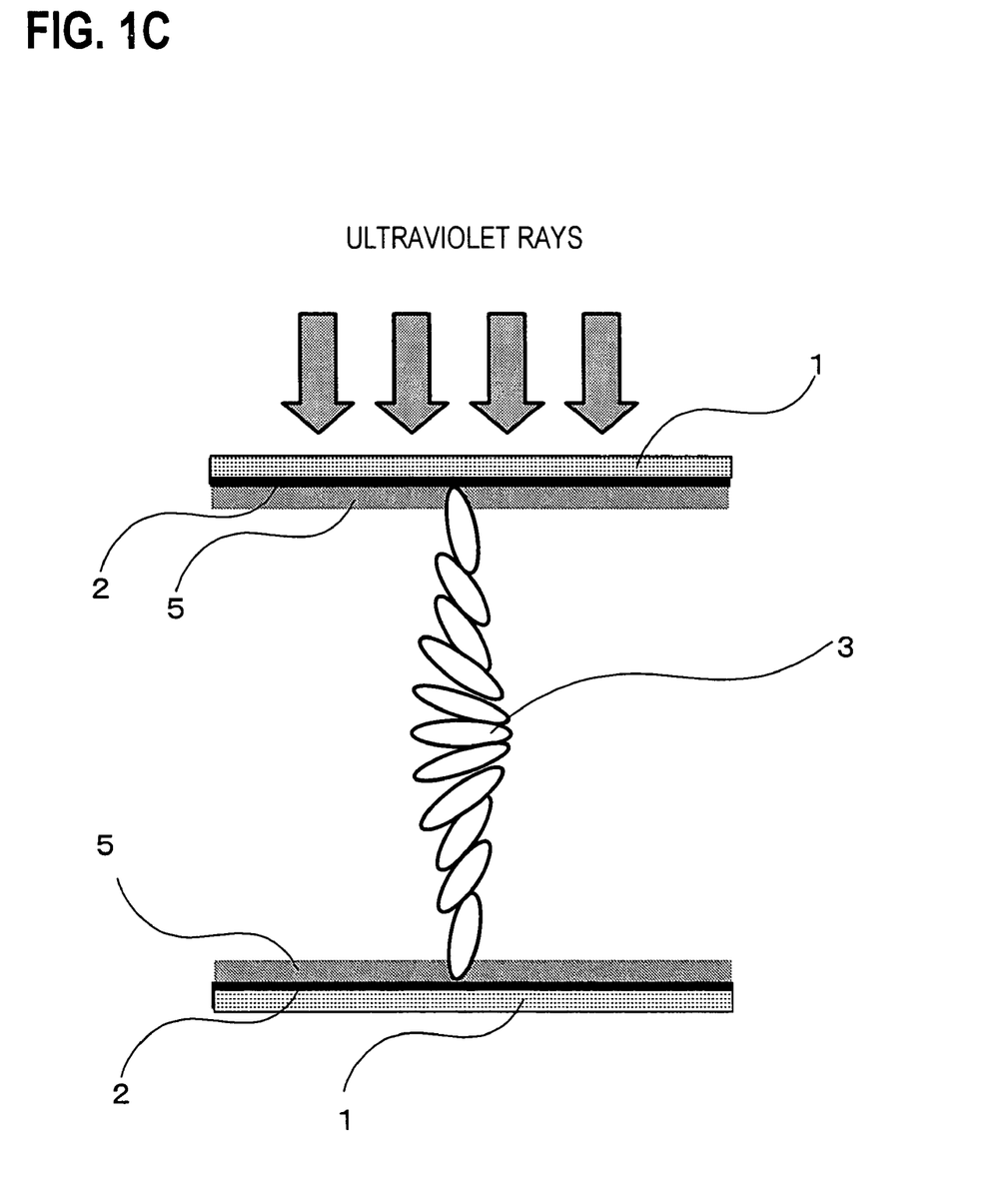
FIG. 1C is a schematic cross-sectional side view depicting a liquid crystal display panel in a state where ultraviolet rays are being irradiated to fix liquid crystal molecules in the splay state with the result that resin films are formed.

If a voltage not lower than $V_{cr}$ is applied in this state, the liquid crystal molecules 3 change to the splay state, as shown in FIG. 1B. If ultraviolet rays are irradiated, for example, as shown in FIG. 1C, while maintaining this state (that is, while voltage is continuously applied), then resin films 5 made of the polymer are formed, and the alignment state of the liquid crystal molecules 3 is fixed.

Figure 2A:
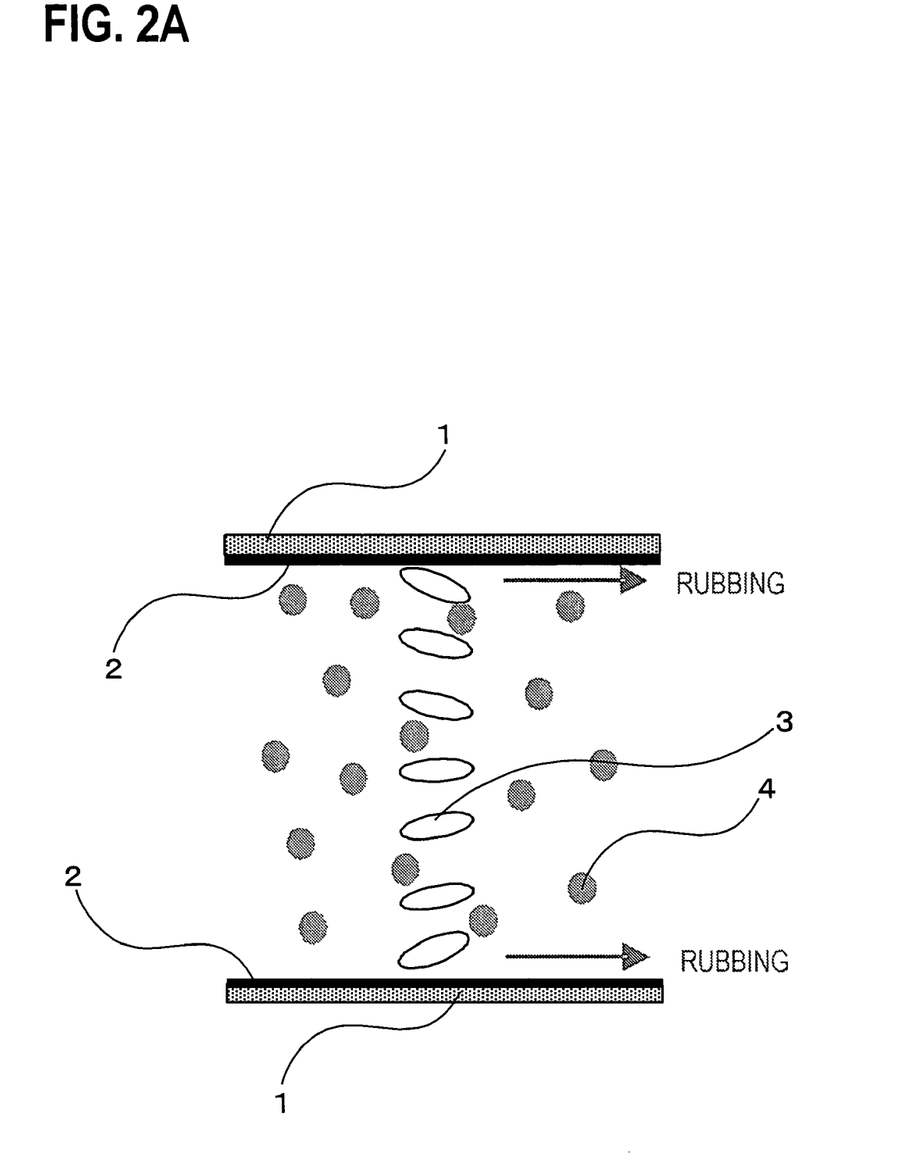
FIG. 2A is a schematic cross-sectional side view depicting liquid crystal molecules in the splay state in a liquid crystal display panel.
Figure 2B:
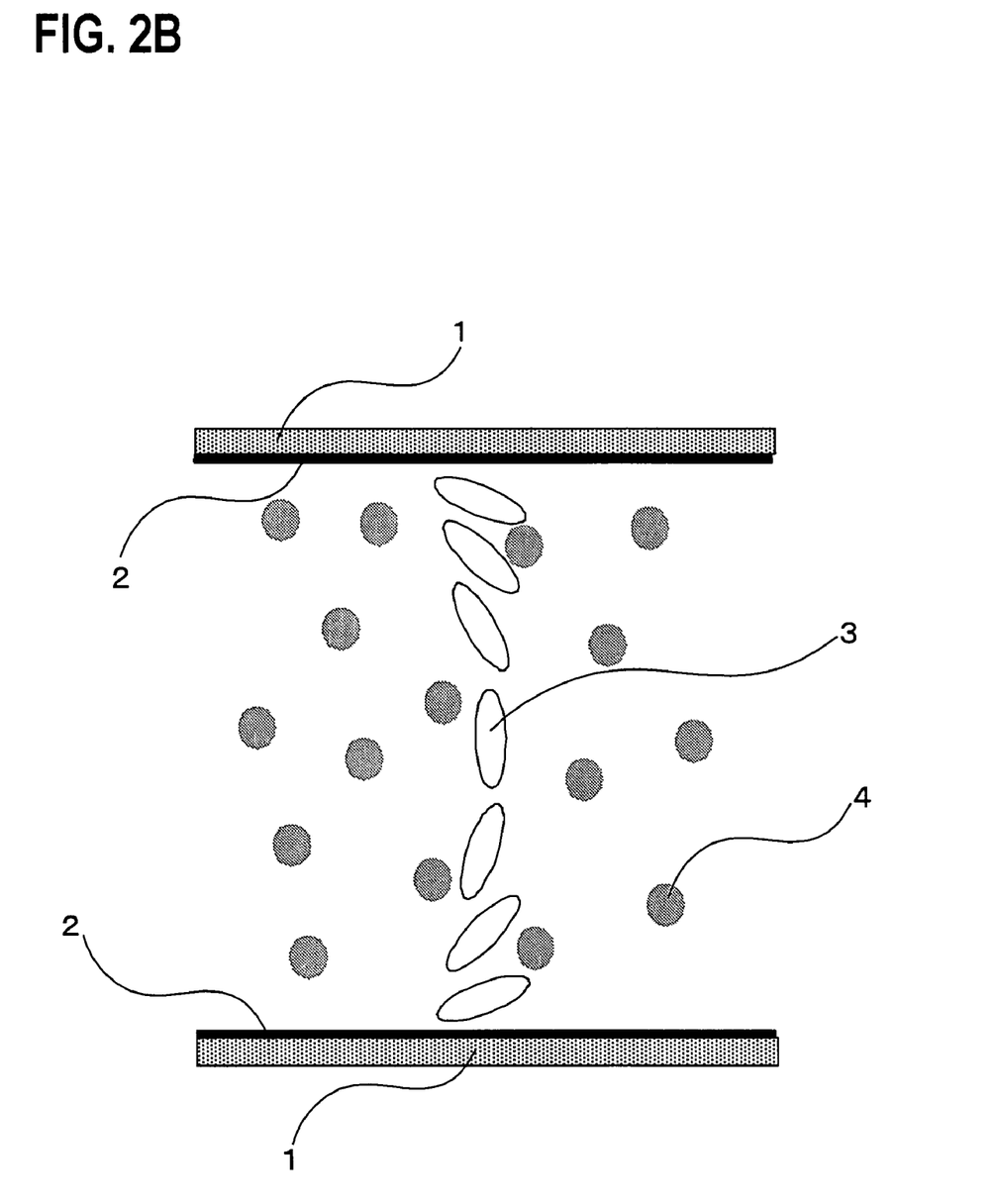
FIG. 2B is a schematic cross-sectional side view depicting liquid crystal molecules in the bend state in a liquid crystal display panel.
Figure 2C:
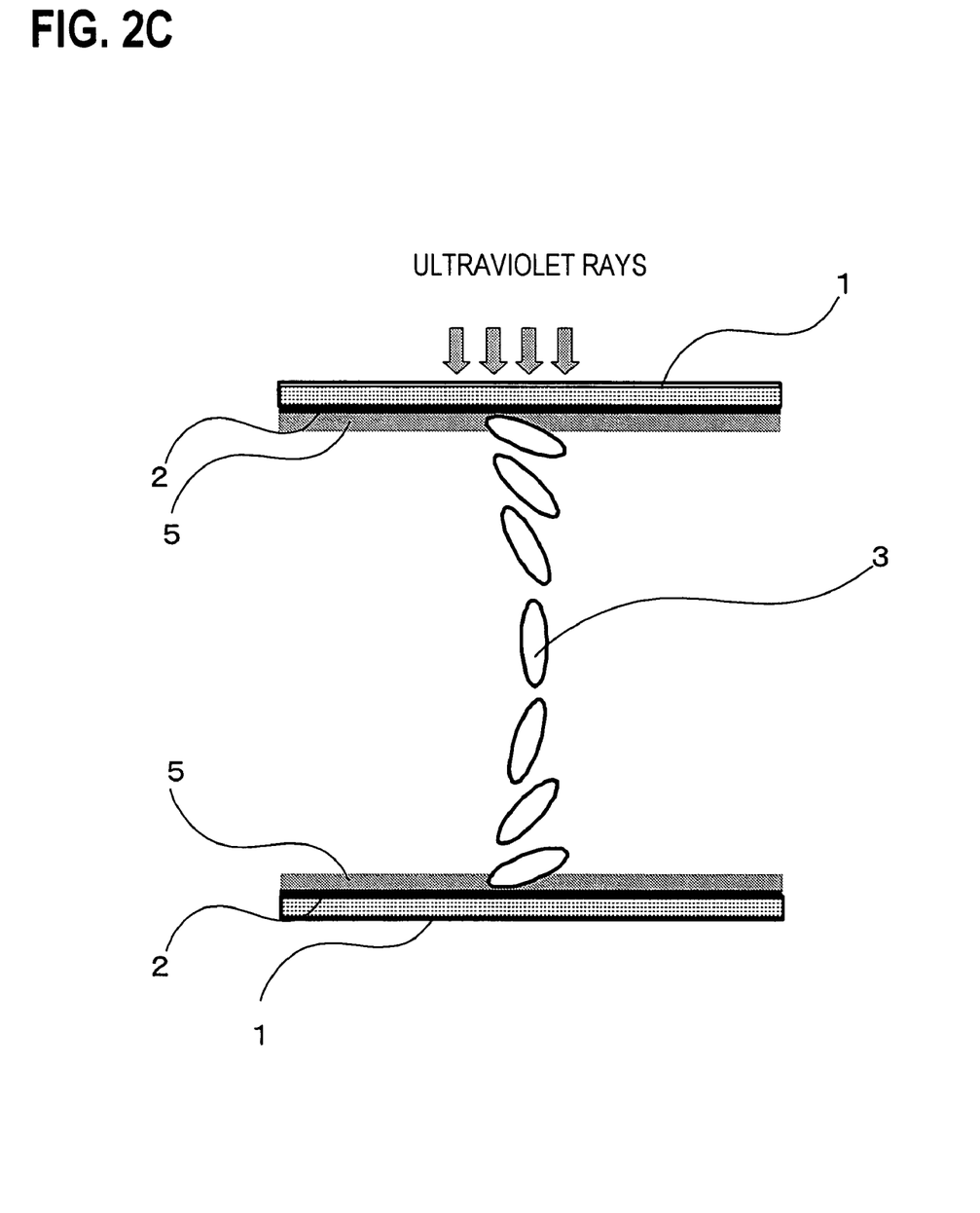
FIG. 2C is a cross-sectional side view depicting a liquid crystal display panel in a state where ultraviolet rays are being irradiated to fix liquid crystal molecules in the bend state, with the result that resin films are formed.

FIGS. 2A, 2B and 2C show the case of liquid crystals having a positive dielectric constant anisotropy. FIG. 2A is a cross-sectional view of a liquid crystal display panel viewed from the side when a pair of horizontal alignment control films 2 are formed on a pair of substrates 1, and have been rubbed so that the rubbing directions are parallel to each other, between which a liquid crystal composition comprising a liquid crystal 3 having a positive dielectric constant anisotropy, and a polymerizable compound 4 which can be polymerized by light, heat or a combination thereof, is filled. In FIG. 2A, the arrows indicate the rubbing direction. In this case, voltage is not applied between the substrates 1. And in this state, the liquid crystal molecules 3 are in the splay state, as shown in FIG. 2A.

If a voltage not lower than $V_{cr}$ is applied in this state, the liquid crystal molecules 3 change to the bend state, as shown in FIG. 2B. If ultraviolet rays are irradiated, for example, as shown in FIG. 2C, while maintaining this state (that is, while voltage is continuously applied), then resin films 5 made of the polymer are formed, and the alignment state of the liquid crystal molecules 3 is fixed.

However, a large quantity of monomers must be added to fix the alignment after the alignment transition, and the problems here include phenomena that monomers do not dissolve sufficiently into the liquid crystal, and coagulation is generated at polymerization, with the result that fixing the alignment after the transition without dropping the display quality is difficult. Also with this method, the range where retardation can be changed is small, and the change of transmittance with respect to the change of the applied voltage is small.

SUMMARY OF THE INVENTION

It is an object of the present invention to provide a liquid crystal display device which can solve these problems and present a high-speed response. Other objects and advantages of the present invention shall be clarified in the description herein below.

One aspect of the present invention provides a liquid crystal display device obtained by disposing, between two parallel substrates on which a pair of electrodes are formed, two alignment control films, and a liquid crystal composition comprising a liquid crystal and a polymerizable compound that can be polymerized by light, heat or a combination thereof, and then polymerizing the polymerizable compound, wherein the liquid crystal is a liquid crystal having a negative dielectric constant anisotropy, the alignment control films are vertical alignment control films having been subjected to rubbing processing so that the rubbing directions are parallel to each other, and when voltage is not applied, only liquid crystal molecules in a specific area in a pixel present a splay alignment.

It is preferable that the polymerization is performed only for a specific area in a pixel at a stage when the bend alignment of liquid crystal molecules at no voltage application has been shifted to a splay alignment by applying a predetermined voltage.

Another aspect of the present invention provides a liquid crystal display device obtained by disposing, between two parallel substrates on which a pair of electrodes are formed, two alignment control films, and a liquid crystal composition comprising a liquid crystal and a polymerizable compound that can be polymerized by light, heat or a combination thereof, and then polymerizing the polymerizable compound, wherein the liquid crystal is a liquid crystal having a positive dielectric constant anisotropy, the alignment control films are horizontal alignment control films having been subjected to rubbing processing so that the rubbing directions are parallel to each other, and when voltage is not applied, only liquid crystal molecules in a specific area in a pixel present the bend alignment.

It is preferable that the polymerization is performed only for a specific area in a pixel at a stage when the splay alignment of liquid crystal molecules at no voltage application has been shifted to the bend alignment by applying a predetermined voltage.

By the above aspects of the invention, a liquid crystal display device having a high-speed response can be implemented.

In both of the above aspects, it is preferable that polymerization is performed by light, heat or a combination thereof for an area other than the specific area after the above-described polymerization, that the specific area is an area where an image is not displayed, that the specific area is on an image display section and is in the form of dots and/or lines, that the specific area is on a black matrix, that protrusions or slits of electrodes for controlling the alignment of the liquid crystal do not exist, that the polymerizable compound comprises a multi-functional polymerizable compound with two or more functions, that the polymerizable compound comprises a methacrylate monomer, and that the polymerizable compound comprises trimethylol propane trimethacrylate.

By the present invention, a liquid crystal display device having a high-speed response can be implemented.

DESCRIPTION OF THE PREFERRED EMBODIMENTS

Embodiments of the present invention will now be described with reference to the drawings and examples. These drawings, embodiments and description are for showing examples of the present invention, and are not for limiting the scope of the present invention. Needless to say, other embodiments are included in the scope of the present invention as long as they conform to the essential character of the present invention. In the drawings, the same reference symbol indicates the same composing element. The same reference symbol is used for both the vertical alignment control film and horizontal alignment control film. In the same way, the same symbol is used for both a liquid crystal (or liquid crystal molecules) having a negative dielectric constant anisotropy and a liquid crystal (or liquid crystal molecules) having a positive dielectric constant anisotropy.

The liquid crystal display device according to the present invention is obtained by disposing, between two parallel substrates on which a pair of electrodes are formed, two alignment control films, and a liquid crystal composition comprising a liquid crystal and a polymerizable compound that can be polymerized by light, heat or a combination thereof, and then polymerizing the polymerizable compound.

At this time, in the case where a liquid crystal having a positive dielectric constant anisotropy, is used, the alignment control films are horizontal alignment control films having been subjected to rubbing processing so that the rubbing directions are parallel to each other, and only liquid crystal molecules in a specific area in a pixel present the bend alignment, when voltage is not applied.

In order to implement this structure, horizontal alignment control films having been subjected to rubbing processing so that the rubbing directions are parallel to each other, are used as the alignment control films, and at a step where the splay alignment of the liquid crystal molecules at no voltage application has shifted to the bend alignment by applying a predetermined voltage, the above mentioned polymerization is performed only for a specific area in a pixel. This predetermined voltage can be arbitrarily selected, depending on the actual situations, from the voltages by which the splay alignment of the liquid crystal molecules at no voltage application shifts to the bend alignment.

For the material of alignment control films, any known material may be used, but the rubbing directions must be parallel to each other. If the rubbing directions are not parallel, such as perpendicular to each other, or are inversely parallel (the rubbing directions being parallel in opposite directions), the desired initial liquid crystal alignment cannot be obtained.

The above mentioned polymerization is performed by light, heat or a combination thereof, but using light is preferable, and ultraviolet rays are particularly preferable. Hereafter, the case of irradiating ultraviolet rays will be described.

Whether the splay alignment of liquid crystal molecules at no voltage application has been shifted to the bend alignment or not can easily be determined in advance by experiments or the like. The degree of polymerization is not particularly restricted, and can be determined arbitrarily according to the actual situations. Irradiation of ultraviolet rays is advantageous, because preferable irradiation conditions can be easily selected through such factors as the wavelength of ultraviolet rays, irradiation energy and irradiation time.

Figure 3:
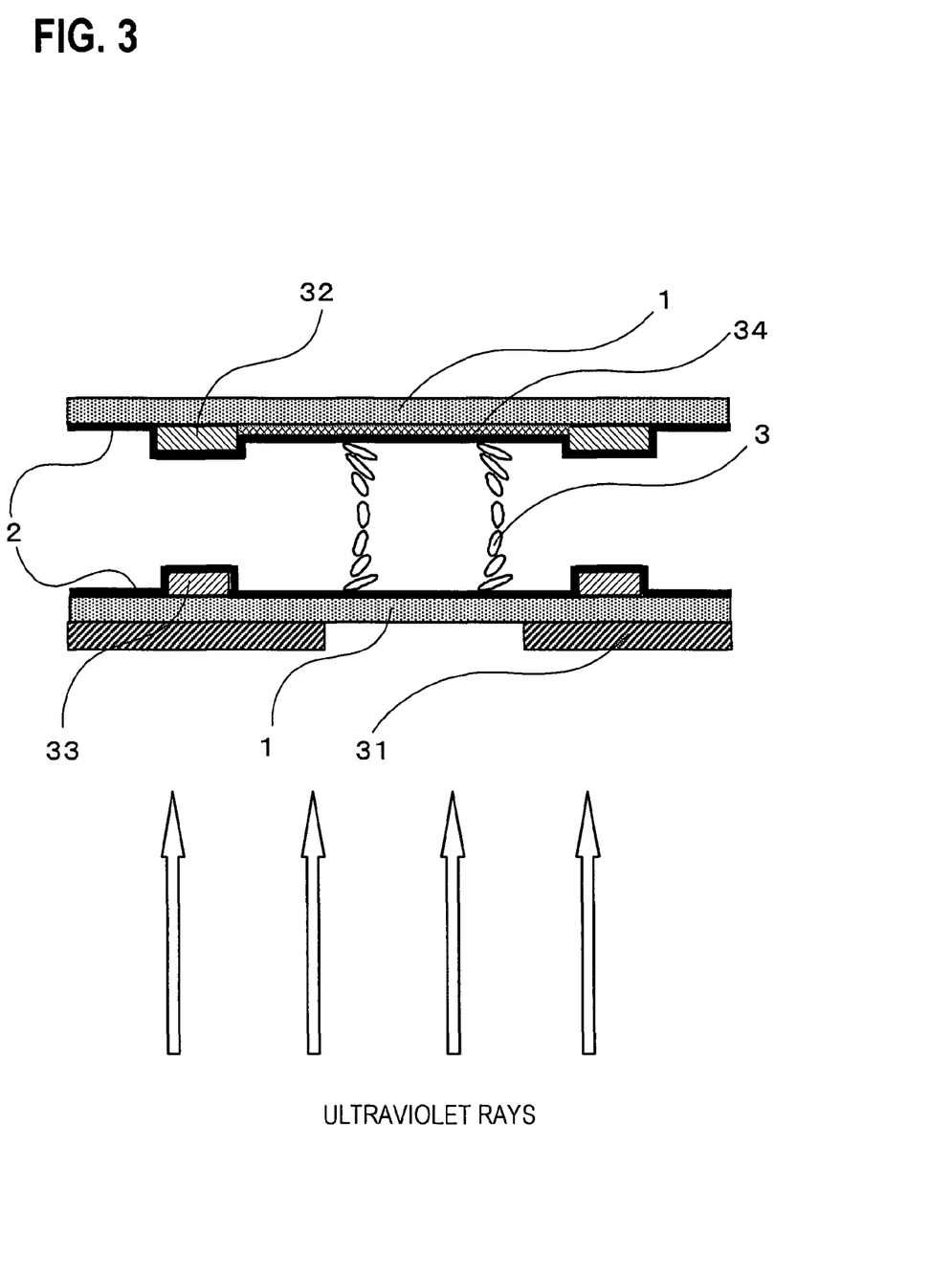
FIG. 3 is a schematic cross-sectional side view depicting a liquid crystal display panel in a state where ultraviolet rays are being irradiated using a mask to fix liquid crystal molecules in the bend state only for a specific area, so that resin films are formed.

Ultraviolet rays are irradiated using a mask 31, for example, as shown in FIG. 3. FIG. 3 shows a state where liquid crystal molecules are set to the bend state by applying voltage, and irradiated with ultraviolet rays. In the case of using ultraviolet rays, irradiation is carried out from the substrate surface which does not have a layer to absorb ultraviolet rays, such as color filter (CF) 34 and black matrix (BM) 32 as shown in FIG. 3. The numeral 33 in FIG. 3 shows a thin film transistor (TFT). The alignment control films are indicated by numeral 2.

In this way, by performing polymerization only for a specific area in a pixel, the liquid crystal molecules in this area can maintain the bend alignment even if the voltage is not more than $V_{cr}$ (e.g. no voltage application state). Then, when voltage is applied, a shift to the bend alignment progresses using this area as a core of alignment transition, even if the liquid crystal molecules of the other areas are in the splay alignment, so a liquid crystal display device having a high-speed response can be implemented.

Alternatively, the specific area of a pixel may be set to a pre-tilted state, or to a state where pre-tilting is greater than the other areas (this area may be called a "high pre-tilt area"). In this case as well, the alignment change speed can be made large, and a liquid crystal display device having a high-speed response can be implemented. In the following description, the effect of polymerizing only a specific area in a pixel is mainly described simply as "maintaining the bend alignment (or the splay alignment)", but the case of having a characteristic of a high pre-tilt area or the case of having both characteristics of a high pre-tilt area and bend (splay) alignment maintained area can also be regarded as an effect of the present invention. If the crystal molecules are initially in the splay alignment (at no voltage application), the degree of pre-tilt is lager as the angle of the liquid crystal molecules that forms with the substrate surface is smaller, and if the crystal molecules are initially in the bend alignment (at no voltage application), the degree of pre-tilt is larger as the angle of the liquid crystal molecules that forms with a direction perpendicular to the substrate face is smaller (in other words, as the angle of the liquid crystal molecules that forms with the substrate face is larger).

If a liquid crystal having a negative dielectric constant anisotropy, is used for the liquid crystal, the alignment control films are vertical alignment control films having been subjected to rubbing processing so that the rubbing directions are parallel to each other, and only the liquid crystal molecules in a specific area in a pixel must present the splay alignment when voltage is not applied.

This structure can be obtained by using vertical alignment control films on which rubbing processing has been carried out so that the rubbing directions are parallel to each other as the alignment control films, and performing the above mentioned polymerization only for a specific area in a pixel at a stage when the bend alignment of liquid crystal molecules at no voltage application has been shifted to the splay alignment by the application of a predetermined voltage.

The rubbing directions of the alignment control films, polymerization conditions and ultraviolet rays irradiation conditions are the same as the case of using a liquid crystal having a positive dielectric constant anisotropy for the liquid crystal. For the material of the alignment control films, any known material can be selected if it is for vertical alignment control films.

By performing polymerization only for a specific area in a pixel, the liquid crystal molecules can maintain the splay alignment in this area even at a voltage not more than $V_{cr}$ (e.g. voltage not applied state). Or a high pre-tilt area can be created. By this, a shift to the splay alignment is progressed using this area as a core of alignment transition, even if the liquid crystal molecules of the other areas are in the bend alignment, so a liquid crystal display device having a high-speed response can be implemented.

Figure 6:
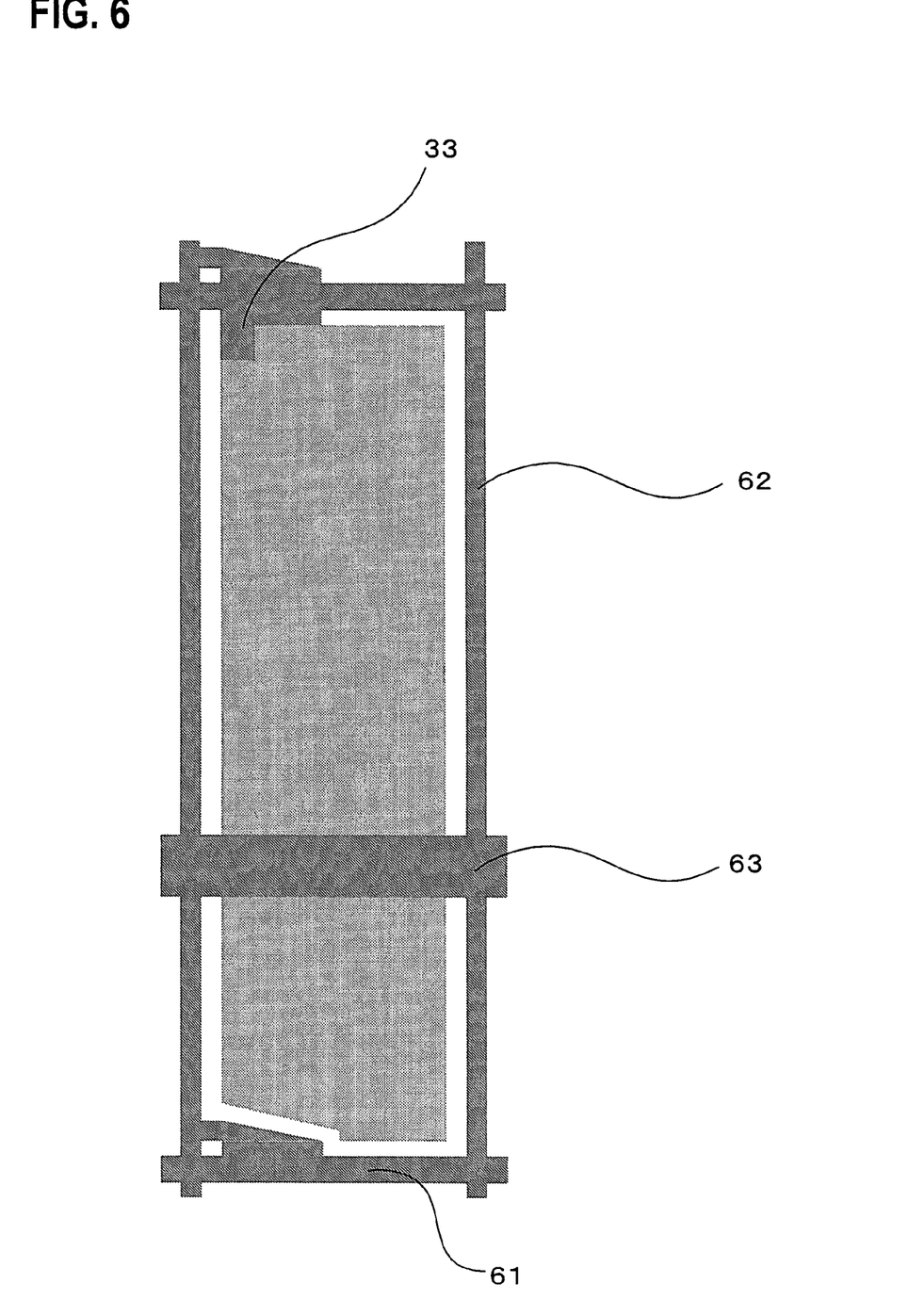
FIG. 6 is a schematic plan view depicting a pixel.

In the above case, the specific area of a pixel can be determined arbitrarily as long as it is within the essential character of the present invention. Here, "a pixel" includes a portion on a non-display area, such as a gate bus line 61, data bus line 62, TFT 33 and auxiliary capacity electrode 63, as shown in FIG. 6.

In the area where the polymerization has been performed, the liquid crystal molecules show an alignment behavior which is different from the other areas, and the color or the like may look different, so it is preferable that this specific area is created in a location which is not outstanding. This means that this specific area is preferably a part of a non-display area. In the case of COT (Color filter On thin film Transistor), for example, CF is often formed on the same side as TFT, on which BM is formed, so if this specific area is formed on BM and ultraviolet rays are irradiated from the substrate side where CF does not exist, the structure of the present invention can be easily implemented without decreasing the aperture rate of pixels. The shape of the specific area in this case is not particularly limited, and may be of any shape, such as lines or dots.

If this specific area is on an image display section, or includes an area on an image display section, the color or the like of the polymerized area may look different from the other areas, so it is preferable that this area is formed in dots and/or lines so as not to stand out. The size of a dot, thickness of a line, and the number of dots and/or lines can be arbitrarily determined considering the influence on the image quality of the liquid crystal display device.

Figure 7:
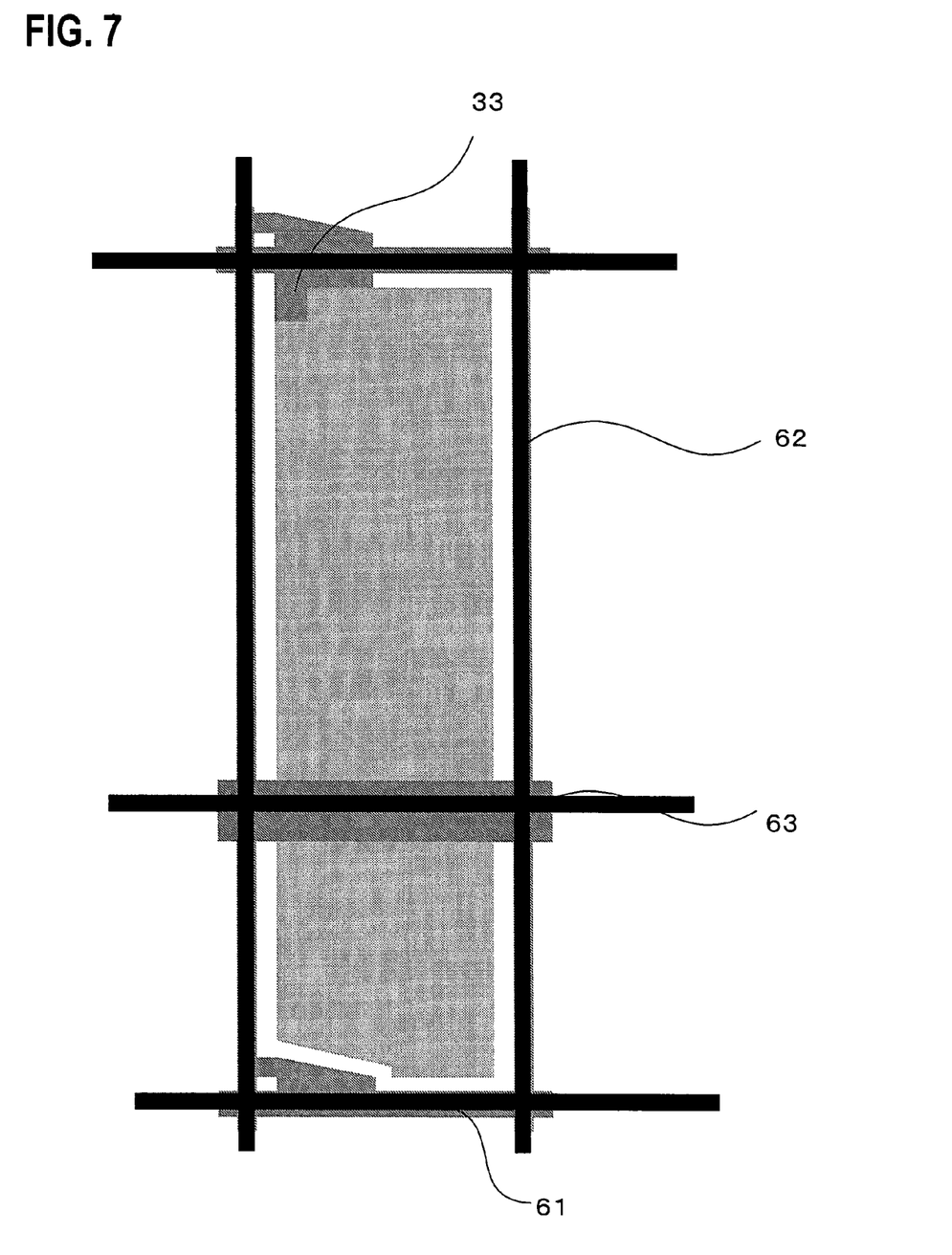
FIG. 7 is a schematic plan view depicting an example of a pixel showing the specific area according to the present invention.
Figure 8:
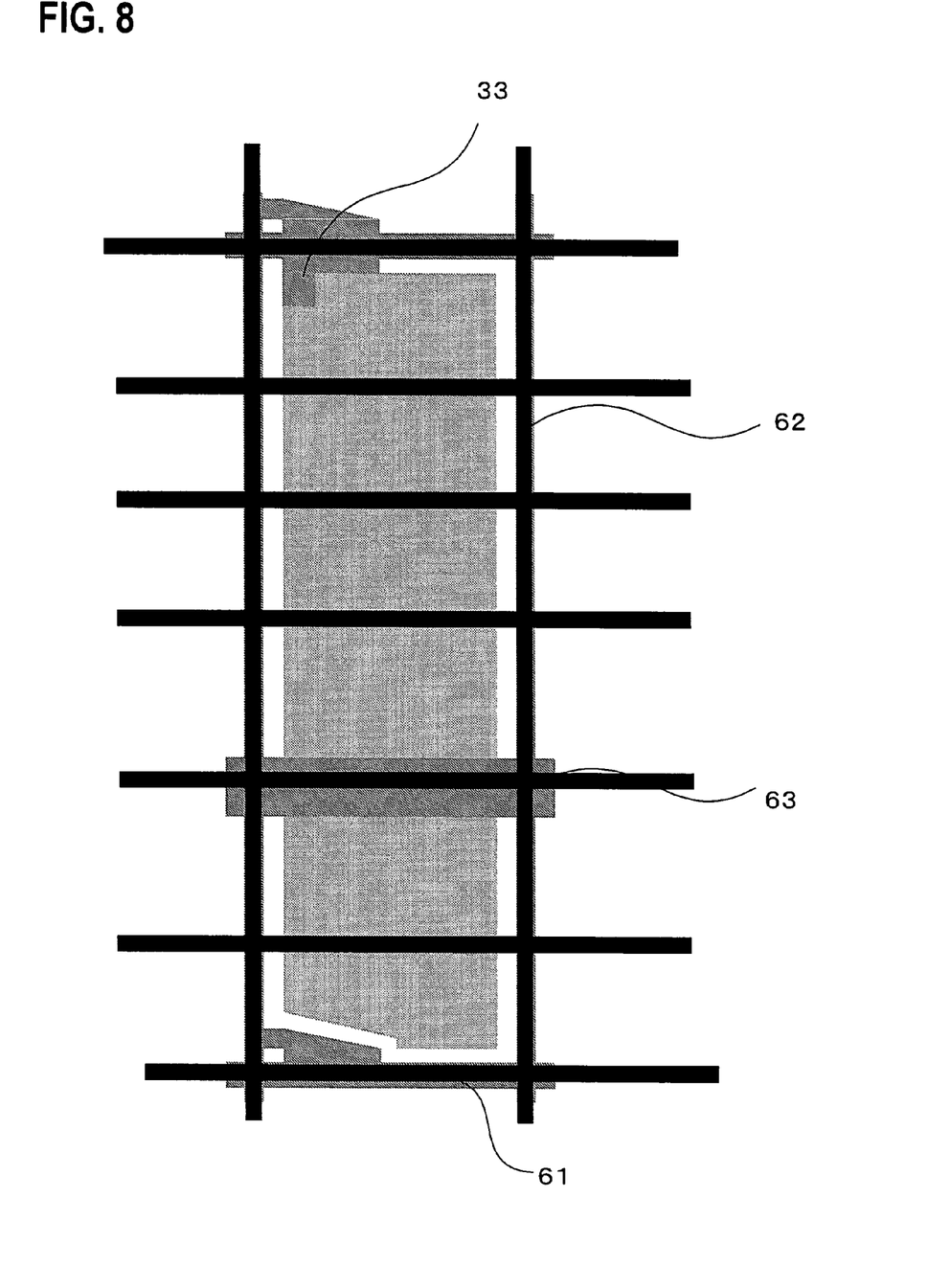
FIG. 8 is a schematic plan view depicting an example of a pixel showing the specific area according to the present invention.
Figure 9:
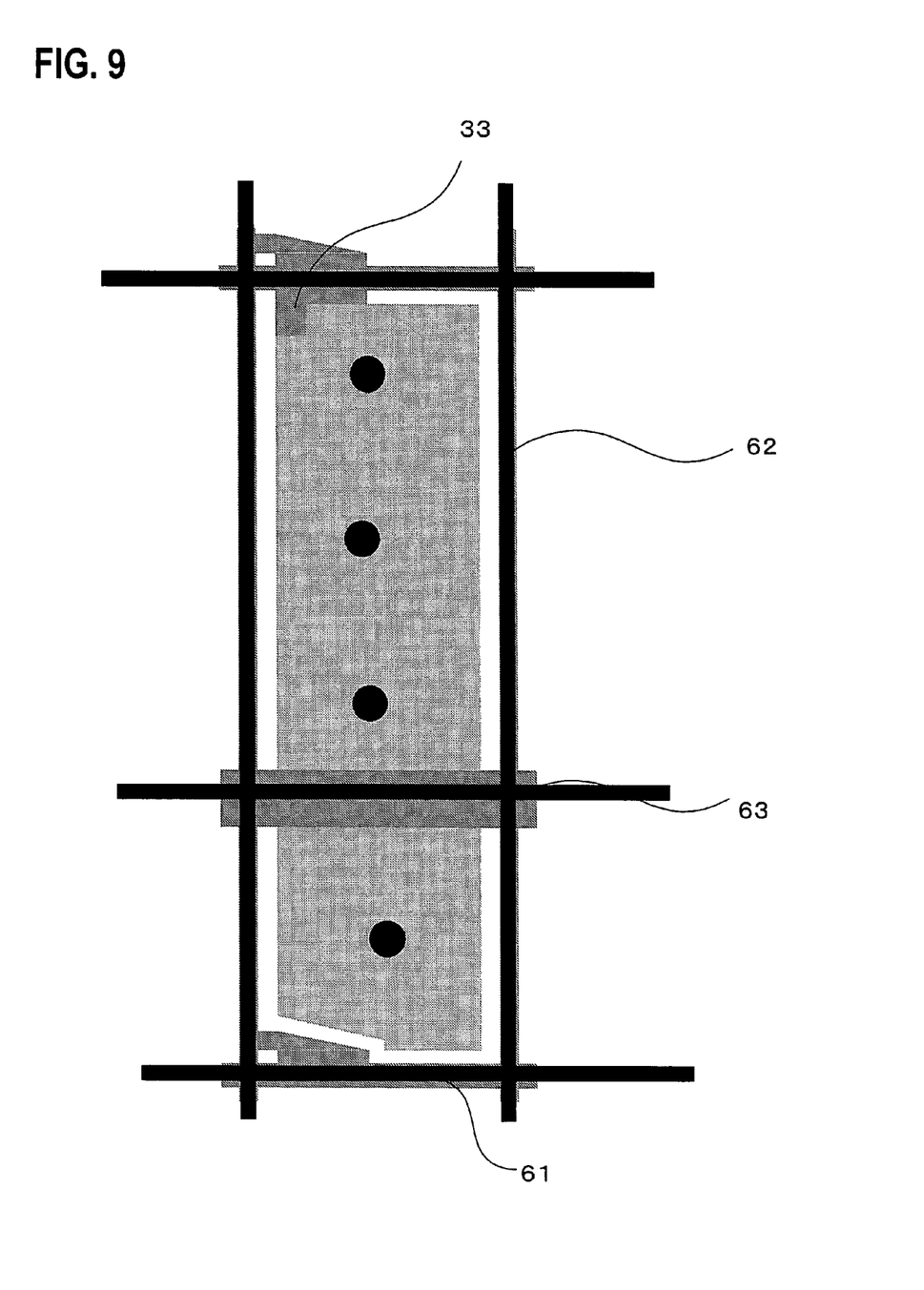
FIG. 9 is a schematic plan view depicting an example of a pixel showing the specific area according to the present invention.

FIG. 7 to FIG. 9 show examples. In the drawings, portions filled in black are the specific areas referred to in the description.

For the configuration of the present invention, it is unnecessary to form protrusions and/or slits for electrodes to control the alignment of the liquid crystal, which are used for the MVA (Multi-domain Vertical Alignment) mode. These protrusions and slits may be formed if desired, but it is preferable to form the specific area avoiding portions near the protrusions and slits for electrodes. This is because differences in color or the like stand out more easily.

Whether dots and/or lines are acceptable and whether the specific area is not near the protrusions and slits for electrodes can be confirmed by actually assembling a liquid crystal display panel and checking the image quality.

After performing the polymerization, it is preferable that the polymerizable compound existing in areas other than the specific area is polymerized in a state which has little influence on the alignment behavior of liquid crystal molecules so as to stabilize the composition of the liquid crystal layer. If the polymerizable compound existing in areas other than the specific area remains without being polymerized, polymerization progresses in a natural state, which could affect the image quality of a display panel.

For polymerizing the polymerizable compound existing in areas other than the specific area, any method can be used if the method has little influence on the alignment behavior of the liquid crystal molecules. Whether the method used has little influence on the alignment behavior of the liquid crystal molecules can be confirmed by checking that the image quality of the liquid crystal display panel is not affected.

Specifically, there is a method of performing polymerization by light, heat or a combination thereof, in a state where voltage is not applied or where the applied voltage is lower than a previously applied voltage. In this case, conditions can be selected, such as decreasing the irradiation intensity of ultraviolet rays, or decreasing the irradiation time.

In order to carry out polymerization in areas other than specific area, a mask may be used, or polymerization may be performed on the entire surface of the display panel without using a mask. In this case, polymerization, not by irradiating light, but by using heat, can be performed easily. Even when light is irradiated, it may be useful in some cases to disperse the unreacted polymerizable compound into the already reacted area (that is the specific area) by performing heat treatment in advance.

Polymerizing the entire surface may be performed before, or after, or before and after polymerizing the specific areas, but it is most effective to perform polymerization after polymerizing the specific areas when the effect of polymerization of the specific areas is considered. Polymerizing the entire surface may be performed without applying voltage to the liquid crystal layer, whether it is performed before or after polymerizing the specific areas, but if it is carried out while applying a predetermined voltage to the liquid crystal layer, the change speed of alignment can be further increased, and a liquid crystal display device having a high-speed response can be implemented.

The liquid crystal composition according to the present invention comprises the above liquid crystal and polymerizable compound. The liquid crystal composition may also comprise a polymerization initiator or a sensitizer.

The liquid crystal used for the liquid crystal composition according to the present invention is not specifically limited, and any known liquid crystals can be used as long as they conform to the essential character of the present invention. An example of a preferable liquid crystal is a nematic liquid crystal.

The polymerizable compound used for the liquid crystal composition according to the present invention is not specifically limited as long as the polymerizable compound has a polymerizable functional group which can be polymerized by light, heat or a combination thereof, and any known polymerizable compounds that can be used with a liquid crystal in a liquid crystal panel may be used. Monomers and oligomers can be used.

For the polymerizable functional group, groups having photo-functionality, such as an acrylate group, methacrylate group, epoxy group, vinyl group, allyl group and an unsaturated double bond can be enumerated.

In order to facilitate the acquirement of the alignment state of liquid crystal molecules when voltage is applied, it is preferable that this polymerizable compound has a molecular structure which can control the director direction of the liquid crystal molecules. For such a molecular structure, an alkyl chain can be used.

Therefore, for the polymerizable compound according to the present invention, a compound having a polymerizable functional group, such as an acrylate group and a methacrylate group for acrylic esters, methacrylic esters, etc., an epoxy group, vinyl group and allyl group can be used, for example.

Generally, it is preferable that the liquid crystal composition according to the present invention comprises a multifunctional polymerizable compound having two or more functions. This is because crosslinking structures are created so that the alignment state of the liquid crystal molecules at a voltage application can be securely maintained.

More specifically, a methacrylate monomer, which has a high solubility to a liquid crystal, is preferable as a polymerizable compound according to the present invention. Examples are dimethacrylate monomers, and trimethylol propane trimethacrylate. Trimethylol propane trimethacrylate (TMPT) the solubility of which to a liquid crystal is several % by weight is the most preferable.

It is considered that when such a polymerizable compound is polymerized, resin films made of the polymer are formed in contact with the liquid crystal layer, and these resin films play a role of controlling the alignment state of the liquid crystal molecules.

In this way, the alignment of liquid crystal molecules after the transition can be uniformly fixed without generating precipitation of the polymerizable compound in the liquid crystal or coagulation during polymerization.

EXAMPLES

Now examples of the present invention will be described.

Example 1

Example 1 is an application of the present invention to a TFT type liquid crystal display device. For the liquid crystal, a nematic liquid crystal having a positive dielectric constant anisotropy is used. The alignment control films are horizontal alignment control films. A 1.5% by weight of TMPT has been added to the liquid crystal composition. In a state where a 20V AC voltage is applied to the entire surface of a panel, a predetermined time elapses and the alignment of the liquid crystal molecules is shifted from the splay state to the bend state. In this state, ultraviolet rays are irradiated from the TFT 33 side via a mask 31, as shown in FIG. 3. The counter substrate side has CF 34, so it is inappropriate to irradiate from this side for the present purpose.

Then, without using a mask, ultraviolet rays are irradiated onto the entire surface of the liquid display panel while voltage is not applied. In this way, a structure, where the bend sate of liquid crystal molecules is maintained only in specific areas in the pixels, can be implemented.

Example 2

As a result of performing the same experiments as in Example 1, using a nematic liquid crystal having a negative dielectric constant anisotropy as the liquid crystal, it was confirmed that the OCS state of the liquid crystal molecules was maintained in areas where ultraviolet rays were irradiated even after two weeks, if 1.5% by weight of TMPT was added.

Example 3

Figure 4A:
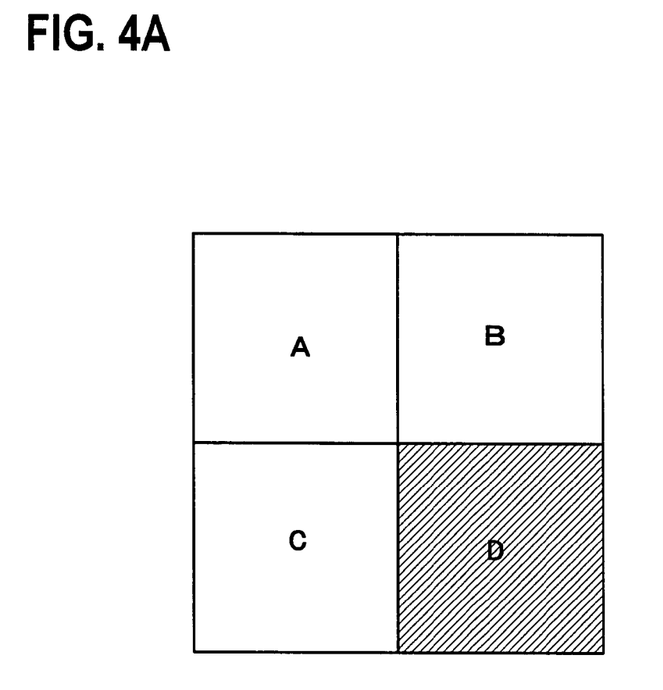
FIG. 4A is a schematic diagram depicting a state of a pixel when the pixel was divided into four (A, B, C, D), and ultraviolet rays were irradiated onto one (D) division as a specific area, and one second elapsed after a voltage of 10V was applied to the state where no voltage was applied.
Figure 4B:
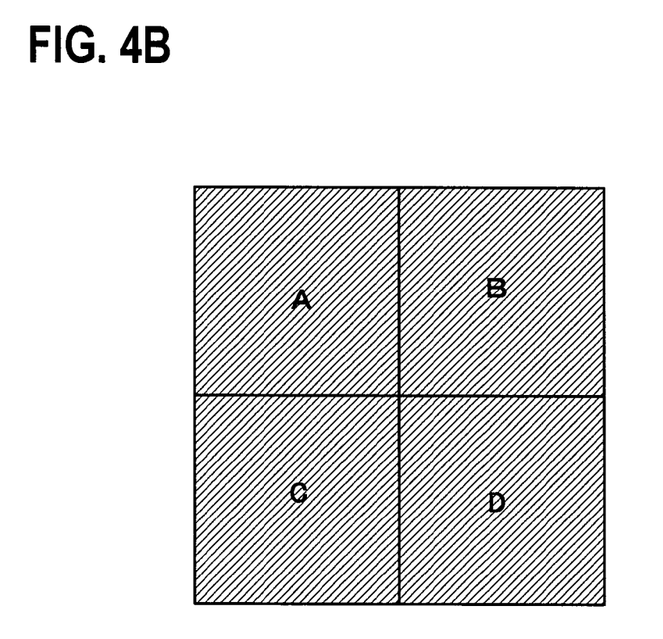
FIG. 4B is a schematic diagram depicting a state of a pixel when the pixel was separated into four (A, B, C, D), and ultraviolet rays were irradiated onto one (D) division as a specific area, and ten second elapsed after a voltage of 10V was applied, to the state where no voltage was applied.

A pixel was divided into four (A, B, C, D) and the same processing as Example 2 was performed on one (D) as the specific area. Then, a voltage of 10V was applied in a state where no voltage had been applied, and as a result, only portion D presented a predetermined color one second later, as shown in the hatched lines in FIG. 4-A, then 10 second later, the other portions also presented the predetermined color, as shown in the hatched lines in FIG. 4-B.

Example 4

Figure 5:
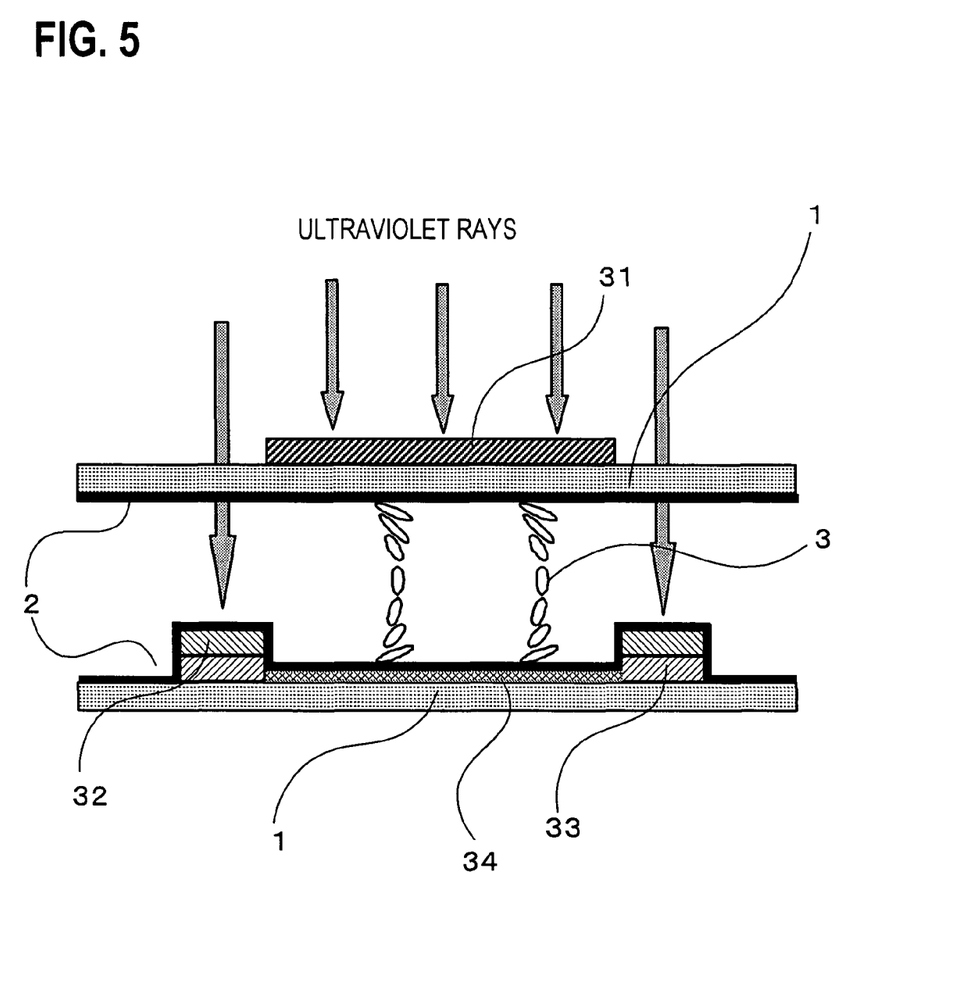
FIG. 5 is a schematic cross-sectional side view depicting a liquid crystal display panel in a state where ultraviolet rays are being irradiated using a mask to fix liquid crystal molecules in the bend state only for a specific area, so that resin films are formed.

This example is the so called "COT structure", wherein, as FIG. 5 shows, the OCB method is used, where CF 34 is formed on the same side as TFT 33, and BM 32 is formed overlapping with TFT 33. In this case, there is no light shielding element, so ultraviolet rays can be irradiated from the counter substrate side.

In a state where the display section was masked by a mask 31 and a predetermined voltage was being applied, ultraviolet rays were irradiated onto TMPT on the BM 32. Then, ultraviolet rays were irradiated onto the entire surface of the liquid crystal display panel without using a mask at no voltage application. In this way, a structure where the bend state of the liquid crystal molecules is maintained only in specific areas in the pixels can be implemented.

In this way, the other liquid crystal molecules in the splay state quickly change using the bend state of the liquid crystal molecules in the non-display section as a core of alignment transition, when the liquid crystal panel is started up, and high-speed response can be implemented. At the same time, retardation change becomes small in the non-display section since the movement of the liquid crystal molecules is controlled by the polymers formed by polymerization, but the actual display is not affected since this is a non-display section, and the sufficiently large retardation change can be implemented in the display section.

Example 5

Splay alignment was examined. After forming high pre-tilt areas to be able to act as a core of the alignment transition in the specific positions of pixels by performing polymerization on the specific areas (polymerization performed only in a specific area in a pixel) using a mask, the mask was removed, and ultraviolet rays were irradiated on the entire surface of the liquid crystal display panel to carry out entire surface polymerization in a state where voltage was being applied.

By this, it was possible to decrease the residual monomers in the panel, and pre-tilting in the entire areas of the display section slightly increased. As a result, the growth speed of the bend alignment increased, and it was possible for the bend alignment generated at the core to quickly spread throughout the entire areas of the pixels. Specifically, the bend transition time became 3 seconds at room temperature, and 15 seconds at −30° C. The bend transition time is a time when a single 1 $cm^2$ pixel completes the alignment transition in the entire area by applying 6V. In the case of a usual OCB, 60 seconds was required at room temperature, and 200 seconds at −30° C.

Example 6

Splay alignment was examined. Prior to forming high pre-tilt areas to be a core of alignment transition in specific positions of pixels by performing specific area polymerization using a mask, the entire surface was polymerized in a state where a mask was not used and voltage was being applied.

By this, it was possible to decrease the residual monomers in the panel beforehand, and pre-tilting in the entire area of the display section slightly increased. As a result, the growth speed of the bend alignment increased, and it was possible for the bend alignment generated at the core to spread throughout the entire area of the pixel quickly.

For the bend alignment as well, effects similar to those of Examples 5 and 6 could be obtained.

The invention claimed is:

1. A liquid crystal display device comprising:
first and second parallel substrates on which a pair of electrodes are formed, first and second alignment control films, and a liquid crystal composition comprising a liquid crystal and a polymerizable compound that can be polymerized by light, heat or a combination thereof, and then polymerizing said polymerizable compound, wherein:
said liquid crystal is a liquid crystal having a positive dielectric constant anisotropy;
said alignment control films are horizontal alignment control films having been subjected to rubbing processing so that the rubbing directions are parallel to each other; and
when voltage is not applied, only liquid crystal molecules in a specific area in a pixel as seen from a direction vertical to the substrate, present bend alignment, or a pre-tilted state, or a state where pretilting is greater than other areas of the pixel, wherein said specific area in the pixel is only a portion of the pixel.

2. The liquid crystal display device according to claim 1, wherein said polymerization is performed only for a specific area in a pixel at a stage when splay alignment of liquid crystal molecules at no voltage application has been shifted to bend alignment by applying a predetermined voltage.

3. The liquid crystal display device according to claim 1, wherein polymerization is performed by light, heat or a combination thereof for areas other than said specific area before, or after, or before and after said polymerization.

4. The liquid crystal display device according to claim 1, wherein an entire surface polymerization for polymerizing one entire pixel in a state where alignment has been shifted by applying a predetermined voltage, is performed along with said polymerization only for said specific area.

5. The liquid crystal display device according to claim 4, wherein said entire surface polymerization is performed before, or after, or before and after said polymerization for said specific area.

6. The liquid crystal display device according to claim 1, wherein said specific area is on a section where an image is not displayed.

7. The liquid crystal display device according to claim 6, wherein said specific area is on a black matrix.

8. The liquid crystal display device according to claim 6, wherein said polymerizable compound comprises a methacrylate monomer.

9. The liquid crystal display device according to claim 1, wherein said polymerizable compound comprises trimethylol propane trimethacrylate.

* * * * *